United States Patent [19]

Bauer et al.

[11] 3,996,351
[45] Dec. 7, 1976

[54] PROCESS FOR ORALLY INCREASING THE BLOOD CALCIUM LEVEL OF ANIMALS

[76] Inventors: Klaus Bauer, Taubergasse 66/2/10, Vienna 17; Franz Sagmeister, Hauslabgasse 8 - 10/11, Vienna 5, both of Austria

[22] Filed: Jan. 30, 1975

[21] Appl. No.: 545,419

[30] Foreign Application Priority Data

Feb. 13, 1974 Austria ............................... 1141/74
July 8, 1974 Austria ............................... 5617/74

[52] U.S. Cl. .................................. 424/153; 424/78; 424/81
[51] Int. Cl.² ................. A61K 33/14; A61K 31/74; A61K 31/78
[58] Field of Search ............... 424/153, 78, 32, 33, 424/81

[56] References Cited

UNITED STATES PATENTS

| | | | |
|---|---|---|---|
| 3,356,570 | 12/1967 | Butcher, Jr. | 424/153 |
| 3,538,214 | 11/1970 | Polli et al. | 424/33 |
| 3,608,063 | 9/1971 | Banker | 424/32 |
| 3,640,741 | 2/1972 | Etes | 424/33 |

FOREIGN PATENTS OR APPLICATIONS 7,932M 9/1968 France ............................ 424/153

OTHER PUBLICATIONS

Chemical Abstracts vol. 20: p. 937 (1926).

*Primary Examiner*—Donald B. Moyer
*Attorney, Agent, or Firm*—Martin A. Farber

[57] ABSTRACT

The preparation comprises a mixture of calcium chloride, a gel-forming polymer, and water. The calcium chloride is in solution in an aqueous gel of said gel-forming polymer. To produce the preparation, a mixture of calcium chloride, a gel-forming polymer, and water is heated to temperatures below 100° C until said calcium chloride and said gel-forming polymer have been completely dissolved.

4 Claims, 1 Drawing Figure

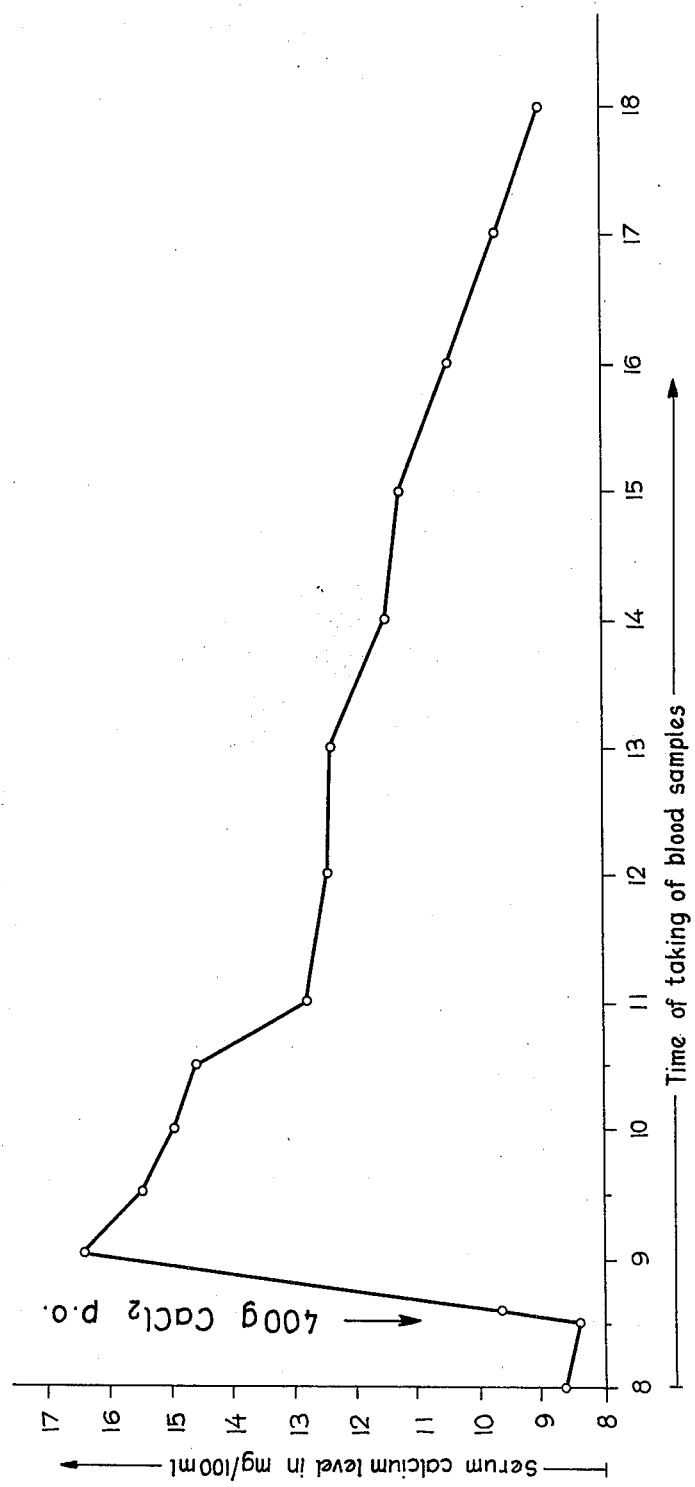

PROCESS FOR ORALLY INCREASING THE BLOOD CALCIUM LEVEL OF ANIMALS

This invention relates to a preparation for increasing the blood calcium level of animals and to a process of producing the preparation.

The calcium metabolism has a high significance in connection with certain diseases, such as birth paresis, osteomalacia, rickets, and tetany, of animals. The body liquids of a cow having a body weight of about 500 kg contain about 8 grams of calcium. Of these 8 g calcium, 3.5 g calcium are contained in the blood and 4.5 g calcium in the tissue liquids. The calcium is being continually incorporated in and extracted from the bone tissue. Calcium is taken up from the feed at a rate of 1 g/h and is dissolved out of the bones at a rate of 1 g/h. At the same time calcium enters the intestine at a rate of 1 g/h and calcium is incorporated into the bones at a rate of 1 g/h. Birth and the lactation beginning at birth result in an acute calcium deficit in the organism because calcium is secreted in the milk at a rate of about 1.5 g calcium per hour.

In some animals, this calcium dificit can be compensated by an increased dissolution of calcium from the bones and under special circumstances by an increased resorption from the intestine. In animals in which this compensation does not take place, the calcium deficit results in a decrease in performance and in diseases which range from subclinical diseases to clinically acute, serious diseases.

For this reason there is a desire for a preparation with which the blood calcium level of animals can be considerably increased so that existing calcium deficits are eliminated or calcium deficits which otherwise would be expected in a foreseeable time are prevented.

In their article "Die Harnprobe nach Sulkowitch in der buiatrischen Diagnostik und der Einflu B peroral verabreichter Calciumpraparate auf den Blutcalciumgehalt und die renale Calciumausscheidung" (Wien. tierarztl. Mschr. 1963, pages 1045–1065), E. Glawischnig and F. Sagmeister have discussed the influence of calcium carbonate, calcium borogluconate, and calcium chloride on the blood calcium level of animals. Based on clinical experiments, they have found that calcium chloride is highly superior to the two other calcium compounds tested as regards the resorption from the rumen, stomach, and intestine and that the blood calcium level can be increased quickly by a peroral and intraruminal adminstration of the readily soluble calcium chloride.

On the other hand, calcium chloride cannot be administered perorally in the form of a simple aqueous solution because the latter would result in cauterization in the mouth cavity and pharynx of the animals being treated. For this reason and owing to the bitter taste of the calcium chloride solution, E. Glawischnig and F. Sagmeister have proposed to administer the preparation only through a catheter extending into the stomach, possibly through the nose and pharynx.

In view of the above it is an object of the invention to provide a preparation which serves to increase the blood calcium level of animals and which enables a considerable increase of the blood calcium level within very short time (half an hour) by a simple, peroral administration of the preparation. The preparation according to the invention is characterized in that it consists of an aqueous mixture of calcium chloride and a gel-forming polymer. A preparation which has proved particularly desirable in practice contains calcium chloride in an amount of 10–40% by weight, preferably 20% by weight, and desirably contains polymer in an amount of 5–20% by weight, preferably 10% by weight. Examples of preferred gel-forming polymers are, inter alia, polyvinylalcohol, polyethyleneglycol, acrylic acid polymer and carboxymethylcellulose. In producing the preparation it is desirable to provide an aqueous mixture which contains calcium chloride, preferably addes as the hexahydrate, in an amount of 10–40% by weight, preferably 20% by weight, and a gel-forming polymer in an amount of 5–20% by weight, preferably 10% by weight, and to heat said mixture at temperatures below 100° C until the ingredients have completely dissolved.

In the preparation according to the present invention, calcium chloride is incorporated in a protective gel an for this reason does not result in cauterization when the preparation is administered perorally. On the other hand, the excellent resorbability of calcium chloride and its high activity to increase the blood calcium level are preserved.

In practice it has proved particularly desirable to cause the aqueous mixture of calcium chloride and the gel-forming polymer to swell the heat treatment.

In certain cases it will be desirable to provide a mixture of water and gel-forming polymer and to cause said mixture to swell before the calcium chloride is added and the resulting mixture is heat-treated.

Alternatively, the preparation may be produced in a process in which a solution of calcium in water is heated to a temperature below 100° C, preferably 95° C, and the gel-forming polymer is added with stirring to said solution which is at said temperature, whereafter the resulting mixture is heat-treated.

Some non-limiting examples of the process according to the invention and the use of the preparation according to the invention will be described hereinafter.

EXAMPLE 1

40 kg calcium chloride hexahydrate are dissolved in 50 l water. 10 kg polyvinylalcohol having an ester value of 8 mg KOH per g polyvinylalcohol are gradually added to the solution. After swelling for three days, the mixture is heated to 90° C and held at this temperature for 1½hours for a completer dissolution. The finished preparation contains 20% by weight calcium chloride.

EXAMPLE 2

14 g polyvinylalcohol havng an ester value of 13 mg KOH per g polyvinylalcohol into 63 l water. After swelling for three days, 23 kg anhydrous calcium chloride are added to the mixture, which is then heated in a water bath until the ingredients have been completely dissolved.

EXAMPLE 3

40 kg polyethyleneglycol having a degree of ppolymerization of 4000 and 40 kg calcium chloride hexahydrate are jointly stirred into 20 l water. The mixture is heated in a water bath until the ingredients have been completely dissolved after about 1½hours.

EXAMPLE 4

10 kg acrylic acid polymer (a 1% aqueous solution of said polymer at pH 6 has a viscosity of 30,000 centipoise at 20° C) and 20 kg anhydrous calcium chloride are jointly stirred into 70 l water. The mixture is heated in a water bath until the ingredients have been completely dissolved.

EXAMPLE 5

In the procedure described in Example 4, 15 kg acrylic acid polymer, 25 kg anhydrous calcium chloride, and 60 l water are used to produce the preparation according to the invention.

EXAMPLE 6

40 kg calcium chloride hexahydrate are dissolved in 50 l water. The solution is heated to 95° C and 10 kg polyvinylalcohol having an ester value of 8 mg KOH per g polyvinylalcohol are gradually stirred into the solution. The mixture is stirred at 95° C until the ingredients have been completely dissolved after 1½ hours. The finished preparation contains 20% by weight calcium chloride.

EXAMPLE 7

40 kg calcium chloride hexahydrate are dissolved in 20 l water and the soluton is hearted in a water bath to 95° C. 40 kg polyethyleneglycol having a degree of polymerization of 4000 are stirred into the hot solution. The mixture is further heated in the water bath until the ingredients have been completely dissolved after about 1½ hours.

EXAMPLE 8

A solution of 20 kg anhydrous calcium chloride in 70 l water is provided and 10 kg acrylic acid polymer (a 1% aqueous solution of the polymer at pH 6 has a viscosity of 30,000 centipoise at 20° C) are stirred into said solution when the latter has been heated to 95° C. The mixture is then heated in a water bath with stirring until the ingredients have been completely dissolved.

EXAMPLE 9

This example was carried out to examine the influence of the preparation produced according to Example 1 on the calcium level in the serum of a bovine animal having a body weight of about 500 kg. The serum calcium level of the bovine animal was determined by the complexometric method of Baron and Bell modified according to Appleton et al. The serum calcium level amounted to 8.6 mg/100 ml at 8 hours and decreased to 8.4 mg/100 ml unitl 8.30 hours. At 8.30 hours, 400 g calcium chloride in the form of the preparation produced according to Example 1 (2 kg) were perorally administered to the bovine animal. The serum calcium level increased to 9.7 mg/100 ml during the next quarter of an hour and reached its highest value of 16.6 mg/100 ml at 9 hours, half an hour after the administration. During the following 9 hours the serum calcium level exhibited an approximately linear decrease to 9 mg/100 ml. This was found from samples which were initially taken at half-hour intervals and then at 1 hour intervals. The change of the serum calcium level with time is represented as a graph on the accompanying drawings.

The infuence of the preparations produced according to Examples 2 to 8 on the serum calcium level was also examined. The blood calcium level was determined by the method stated in Example 9. The experiments indicated that the activity was substantially in accordance with the statements made in connection with Example 9.

The bovine animal did not oppose the administration of the preparation according to the invention and cauterization effects in the mouth cavity or pharynx could not be detected.

The use of the preparation produced according to the invention is not restricted to bovine animals and the preparation can be administered with equally good success to other animals other than human beings, such as horses, pigs, sheep.

What is claimed is:

1. In the method of orally administering a liquid composition containing calcium chloride to an animal for increasing the blood calcium level of the animal in need thereof, the improvement which protects the oral cavity of the animal against cauterization comprising orally administering to said animal a mixture of 10–40% by weight of calcium chloride, 5–20% by weight of gel-forming polymer and water, said calcium chloride being solvatized in an aqueous gel of said gel-forming polymer to contain said calcium chloride.

2. A method according to claim 1 wherein said calcium chloride is in the form of calcium chloride hexahydrate.

3. A method according to claim 1 wherein said calcium chloride in in the form of anhydrous calcium chloride.

4. A method according to claim 1 wherein said gel-forming polymer is selected from the group consisting of polyvinylalcohol, polyethyleneglycol, acrylic acid polymer and carboxymethylcellulose.

* * * * *